United States Patent
Crutchfield, III

(10) Patent No.: US 7,883,726 B2
(45) Date of Patent: *Feb. 8, 2011

(54) SKIN CARE COMPOSITIONS WITH BOTANIC SEED OILS

(75) Inventor: Charles E. Crutchfield, III, Eagan, MN (US)

(73) Assignee: Cuticeuticals, Inc., St. Paul, MN (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/270,521

(22) Filed: Nov. 13, 2008

(65) Prior Publication Data

US 2009/0123578 A1  May 14, 2009

Related U.S. Application Data

(60) Provisional application No. 60/987,950, filed on Nov. 14, 2007.

(51) Int. Cl.
*A01N 65/009* (2006.01)

(52) U.S. Cl. ...................................... 424/725

(58) Field of Classification Search ...................... None
See application file for complete search history.

(56) References Cited

U.S. PATENT DOCUMENTS

| | | | | |
|---|---|---|---|---|
| 2005/0244375 A1* | 11/2005 | Leonard et al. | ............ | 424/93.2 |
| 2007/0128301 A1* | 6/2007 | Saltzman et al. | ............ | 424/765 |
| 2007/0243310 A1* | 10/2007 | Leonard et al. | ............. | 426/651 |
| 2007/0281044 A1* | 12/2007 | Mueller et al. | .............. | 424/727 |

* cited by examiner

*Primary Examiner*—Michael V Meller
(74) *Attorney, Agent, or Firm*—Gerald E. Helget; Nelson R. Capes; Briggs and Morgan, P.A.

(57) ABSTRACT

A topical skin care composition with a base skin care composition suitable for application to skin, and blends of botanic seed oils, prepared according to a cold press method. The base skin care composition uses a multivesicular emulsion skin care delivery system as a base skin care composition. A micelle skin care delivery system is another base skin care composition used in the topical composition. The selected base skin care composition has a range of about 99.9% (% w/w) to 98% (% w/w) of the topical skin care composition, and range of about 0.1 (% w/w) to 2% (% w/w) of blends of botanic seed oil having red raspberry seed oil, and plurality of botanic oils selected from the group consisting of the following seed oils: pumpkin seed oil, chardonnay grape seed oil, carrot seed oil, blueberry seed oil, cranberry seed oil, pomegranate seed oil, black cumin seed oil, and black raspberry seed oil.

2 Claims, No Drawings

SKIN CARE COMPOSITIONS WITH BOTANIC SEED OILS

CROSS-REFERENCE TO RELATED APPLICATION

The present application is based on and claims the benefit of U.S. provisional patent application Ser. No. 60/987,950, filed Nov. 14, 2007, the content of which is hereby incorporated by reference in its entirety.

FIELD OF THE INVENTION

The present invention relates to an improved topical skin care composition having a blend of botanic seed oils, prepared according to a cold press method, for treatment of dry skin, rosacea, fine lines and wrinkles, mild eczema and psoriasis, and as an anti-aging skin conditioner. In particular, the invention relates to an improved skin lotion having a blend of botanic seed oils.

BACKGROUND OF THE INVENTION

Soft, supple and flexible skin has a marked cosmetic appeal and is an attribute of normal functioning epidermis. As human skin ages with advancing years, the epidermis can become folded, ridged or furrowed to form wrinkles. These signal loss of youthful appearance and herald the transition to old age. Exposure to excessive doses of sunlight accelerates the transition process. The outer layer of the epidermis (the stratum corneum) can also become dry and flaky following exposure to cold weather or excessive contact with detergents or solvents. Loss of skin moisture thereby results, and the skin begins to lose the soft, supple and flexible characteristics.

These aging and dry effects on the skin can be a source of irritation, pain and great concern for patients. The use of over the counter creams or lotions to treat fine lines and wrinkles, and act as an anti-aging skin conditioner is prevalent in our society. It is estimated that over fifty percent (50%) of women over age 50 use a skin cream or lotion to improve their complexion.

In addition to the aging and drying effects on the skin, skin conditions such as rosacea affect about 10% of the United States population, and there are estimated to be over 45 million sufferers of rosacea worldwide according to the Rosacea Research & Development Institute. Rosacea is a chronic and progressive disorder of the face, characterized by some or all of the following symptoms: extremely sensitive skin, blushing, flushing, permanent redness, burning, stinging, swelling, papules, pustules, broken red capillary veins, red gritty eyes (which can lead to visual disturbances) and in more advanced cases, a disfiguring bulbous nose. There exists a need for more and better types of topical skin compositions for this skin condition, and other skin conditions such as mild eczema and psoriasis.

There are several types of non-prescription (or "over the counter") topical skin compositions to moisturize the skins. While there are several products that moisturize the skin, their effectiveness on conditions such as rosacea, fine lines and wrinkles, mild eczema and psoriasis, and as an anti-aging skin conditioner may be less than acceptable for many patients. There is a need for improved skin compositions for patients where it is not necessary or desirable for the inclusion of a compound that would require a prescription.

An example of a non-prescription skin lotion that provides benefits and advantages in several skin condition areas is CeraVe®, brand of skin lotion, the trademark is registered to Healthpoint, Ltd. DFB Pharmaceuticals, Inc., San Antonio, Tex. CeraVe® brand of skin lotion uses a multivesicular emulsion skin care delivery system formulation described and claimed in U.S. Pat. No. 6,709,663 entitled Multivesicular Emulsion Drug Delivery Systems, to Robert Espinoza, and assigned to Healthpoint, Ltd. The phrase "multivesicular emulsion delivery system" or "multivesicular emulsion skin care delivery system" as used herein and through this patent disclosure refers to a topical skin delivery composition as has been described and claimed in detail in U.S. Pat. No. 6,709,663. The applicant incorporates by reference herein the entire content of U.S. Pat. No. 6,709,663 as though repeated herein.

An example of another non-prescription skin lotion, different than the multivesicular emulsion skin care delivery system in CeraVe® skin lotion, would be a skin lotion that uses a micelle structure delivery system for nourishing layers of the skin. The following is a description of a micelle structure from Wikipedia.org, the free on-line encyclopedia, at http://en.wikipedia.org/wiki/Micelle:

A micelle (rarely micella, plural micellae) is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle centre. This type of micelle is know as a normal phase micelle (oil-in-water micelle). Inverse micelles have the headgroups at the centre with the tails extending out (water-in-oil micelle). Micelles are approximately spherical in shape. Other phases, including shapes such as ellipsoids, cylinders, and bilayers are also possible. The shape and size of a micelle is a function of the molecular geometry of its surfactant molecules and solution conditions such as surfactant concentration, temperature, pH, and ionic strength. The process of forming micellae is known as micellisation and forms part of the phase behavior of many lipids according to their polymorphism.

The ability of a soapy solution to act as a detergent has been recognized for centuries. However it was only at the beginning of the twentieth century that the constitution of such solutions was scientifically studied. Pioneering work in this area was carried out by James William McBain at the University of Bristol. As early as 1913 he postulated the existence of "colloidal ions" to explain the good electrolytic conductivity of sodium palmitate solutions, [McBain, J. W., Trans. Faraday Soc. 1913, 9, 99.] These highly mobile, spontaneously formed clusters came to be called micelles, a term borrowed from biology and popularized by G. S. Hartley in his classic book "Paraffin Chain Salts, A Study in Micelle Formation". [Hartley, G. S., Aqueous Solutions of Paraffin Chain Salts, A Study in Micelle Formation, 1936, Hermann et Cie, Paris.]

Solvation

Individual surfactant molecules that are in the system but are not part of a micelle are called "monomers." In water, the hydrophilic "heads" of surfactant molecules are always in contact with the solvent, regardless of whether the surfactants exist as monomers or as part of a micelle. However, the lipophilic "tails" of surfactant molecules have less contact with water when they are part of a micelle—this being the basis for the energetic drive for micelle formation. In a micelle, the hydrophobic tails of several surfactant molecules assemble into an oil-like core the most stable form of which has no contact with water. By contrast, surfactant monomers are surrounded by water molecules that create a "cage" of molecules connected by hydrogen bonds. This water cage is similar to a clathrate and has an ice-like crystal structure.

Micelles composed of ionic surfactants have an electrostatic attraction to the ions that surround them in solution, the latter known as counterions. Although the closest counterions partially mask a charged micelle (by up to 90%), the effects of micelle charge affect the structure of the surrounding solvent at appreciable distances from the micelle. Ionic micelles influence many properties of the mixture, including its electrical conductivity. Adding salts to a colloid containing micelles can decrease the strength of electrostatic interactions and lead to the formation of larger ionic micelles. This is more accurately seen from the point of view of an effective change in hydration of the system.

Energy of Formation

Micelles only form when the concentration of surfactant is greater than the critical micelle concentration (CMC), and the temperature of the system is greater than the critical micelle temperature, or Krafft temperature. The formation of micelles can be understood using thermodynamics: micelles can form spontaneously because of a balance between entropy and enthalpy. In water, the hydrophobic effect is the driving force for micelle formation, despite the fact that assembling surfactant molecules together reduces their entropy. Broadly speaking, above the CMC, the entropic penalty of assembling the surfactant molecules is less than the entropic penalty of caging water molecules. Also important are enthalpic considerations, such as the electrostatic interactions that occur between the charged parts surfactants.

Inverse Micelles

In a non-polar solvent, it is the exposure of the hydrophilic head groups to the surrounding solvent that is energetically unfavorable, giving rise to a water-in-oil system. In this case the hydrophilic groups are sequestered in the micelle core and the hydrophobic groups extend away from the centre. These inverse micelles are proportionally less likely to form on increasing headgroup charge, since hydrophilic sequestration would create highly unfavorable electrostatic interactions.

Uses

When surfactants are present above the CMC (Critical micelle concentration), they can act as emulsifiers that will allow a compound normally insoluble (in the solvent being used) to dissolve. This occurs because the insoluble species can be incorporated into the micelle core, which is itself solubilized in the bulk solvent by virtue of the head groups' favorable interactions with solvent species. The most common example of this phenomenon is detergents, which clean poorly soluble lipophilic material (such as oils and waxes) that cannot be removed by water alone. Detergents also clean by lowering the surface tension of water, making it easier to remove material from a surface. The emulsifying property of surfactants is also the basis for emulsion polymerization.

Micelle formation is essential for the absorption of fat-soluble vitamins and complicated lipids within the human body. Bile salts formed in the liver and secreted by the gall bladder allow micelles of fatty acids to form. This allows the absorption of complicated lipids (e.g., lecithin) and lipid soluble vitamins (A, D, E and K) by the small intestine within the micelle.

There is a need for an improved skin care composition, such as a skin lotion, that does not need to be available by prescription, and improves upon the benefits of the skin lotion, such as CeraVe® brand of skin lotion, and is well tolerated and accepted by patients as an effective treatment for dry skin, rosacea, fine lines and wrinkles, mild eczema and psoriasis, and as an anti-aging skin conditioner.

SUMMARY OF THE INVENTION

The present invention is an improved topical skin care composition using a base composition suitable for application to skin, and adding blends of botanic seed oils, prepared according to a cold press method, to achieve superior results on patients treated for skin condition such as dry skin, rosacea, fine lines and wrinkles, mild eczema and psoriasis, and as an anti-aging skin conditioner.

In formulating the improved skin care composition, the base skin care composition includes a multivesicular emulsion skin care delivery system as a base skin care composition that can be used in the improved topical composition. A micelle skin care delivery system is another base skin care composition that can be used in the improved topical composition. The selected base skin care composition has a range of about 99.9% (% w/w) to about 98% (% w/w) of the improved skin care composition, and a range of about 0.1 (% w/w) to about 2% (% w/w) of blends of botanic seed oil having red raspberry seed oil, and a plurality of botanic oils selected from the group consisting of the following seed oils: pumpkin seed oil, chardonnay grape seed oil, carrot seed oil, blueberry seed oil, cranberry seed oil, pomegranate seed oil, black cumin seed oil, and black raspberry seed oil.

DETAILED DESCRIPTION OF THE PREFERRED EMBODIMENT

An improved topical of the present invention uses a skin lotion as a base composition suitable for application to skin having a multivesicular emulsion skin care delivery system, prepared according to Espinoza. A preferred skin lotion as a base composition suitable for application to skin having a multivesicular emulsion skin care delivery systems, according to Espinoz, is CeraVe® brand of skin lotion.

Coria Laboratories, Ltd on its web site stated that CeraVe® uses patented multivesicular emulsion skin care delivery technology in CeraVe® skin care products, and has a copyright of 2006. CeraVe® skin lotion is one of those products, and includes the following listed ingredients: purified water, glycerin, caprylic/capric triglyceride, behentrimonium methosulfate and cetearyl alcohol, ceteareth-20 and cetearyl alcohol, ceramide 1, ceramide 3, ceramide 6-11, hyaluronic acid, cholesterol dimethicone, polysorbate 20, polyglyceryl-3 diisostearate, potassium phosphate, dipotassium phosphate, sodium lauroyl lactylate, cetyl alcohol, disodium EDTA, phytosphingosine, methylparaben, propylparaben, carbomer, xantham gum The inventor has improved upon topical skin compositions suitable for application to skin with the addition of blends of botanic seed oils prepared according to a cold press method. The inventor has tested an improved skin care composition of the invention as a lotion on patents with rosacea and on patients as an anti-aging conditioner with wrinkles and fine lines. The favorable results of those treatments are discussed in a latter portion of this patent disclosure.

The use of concentrated seed oils, also referred to as botanic seed oils prepared according to a cold press method, in the improved topical skin care composition acts as natural emollients to prevent dryness and protect the skin, acting as a barrier and healing agent, as well as a soothing and softening agent of the skin. The concentrated seed oils in the improved skin lotion can reduce roughness, cracking and irritation. The use of botanic seed oil emollients nourish the skin with concentrated nutrients that are beneficial in treating conditions of the skin such as dry skin, rosacea, fine lines and wrinkles, and as an anti-aging skin conditioner. The antioxidant properties of botanic seed oils may prove to have some of the most effective rejuvenating properties of any known skin treatment to date. Charles E. Crutchfield, M.D. Assoc. Prof. of Dermatology, University of Minnesota, et al., *The Use of Nature Fresh Cold Pressed Seed Oils for Skin and Personal Care Products—A New Approach* (an article pending publication), incorporated by reference herein, and included in its entirety below:

The Use of Nature Fresh Cold Pressed Seed Oils for Skin and Personal Care Products—A New Approach Arnold S. Leonard, M. D., Ph.D., Mark Mueller and Charles E. Crutchfield III, M.D Why are oils extracted at cold temperature from fruit, herb and spice seeds amazingly good for your skin and superior ingredients for a great variety personal care products?

The short answer is; seeds are the antioxidant and nutrient powerhouses of the plant. They are the mother lode of natural protection mechanisms for the regenerative but fragile plant embryo. Oils extracted at cold temperature contain all the vital nutrients, essential fatty acids, trace minerals like zinc, magnesium and calcium necessary to sustain the plant germ in its first days of life. The plant chemical protection mechanisms of seeds are complex, diverse and biodynamic, involving literally dozens, even hundreds of different plant chemicals that protect the fragile embryo from oxidation, damage from UV light, and the onslaught of a myriad of environmental microorganisms such as fungi and molds. These natural protection mechanisms are so effective the embryo in some seeds have been known to be viable for hundreds of years.

A company on the forefront of the exciting frontier of extracting novel fruit, herb and spice seed oils is Botanic Oil Innovations, Inc., [immunoviva.com.] Using its' proprietary NatureFRESH-Cold Press process, it produces nutrient dense, biodiverse, super potent antioxidant novel fruit, herb and spice seed oils for the dermatology and personal care products industry. Botanic Oil Innovations produces these novel oils from such plants as cranberry, blueberry, raspberry, blackberry, grape, black cumin, milk thistle and pomegranate to mention a few.

Oils extracted from seed using this cold process are raw foods, unadulterated by heat, solvents or additives. The resulting oils have a rich and diverse range of protective phytochemicals that function to protect the seed from oxidation, ultra violet light and to ward off attack from microorganisms. Often these novel fruit, herb and spice seed oils contain the full range of eight different forms of natural vitamin E in the form of tocopherols and tocotrienols, not just the alpha tocopherol (given a bad name by a number of periodicals). And they contain a great variety of other antioxidants, like the carotinoids carotein, lutein and zeaxanthen, cryptozantin and literally hundreds of other plant chemicals like quinones and polyphenolics.

Is there any wonder then that these same protection mechanisms for the plant embryo aren't also good for your body's natural protective covering, the largest organ of your body, your skin? Benefits from these novel oils include protection against skin bacteria, protection from UV light improved antioxidant protection, accelerated healing, increased collagen expression, and increased elasticity and more pliable skin. Botanic Oil Innovations, in conjunction with other Universities, has conducted extensive laboratory testing demonstrating the functional protective values. Here are some things they are researching and finding:

Emolliency

The novel botanical oils are natural emollients. They prevent dryness and protect the skin, acting as a barrier and healing agent, as well as a soothing and softening agent of the skin. They reducing roughness, cracking and irritation and may even assist with retarding fine wrinkles. While water is the best emollient, it evaporates too quickly to be effective unless it is used in conjunction with oils in an emulsion. Natural botanical oil emollients nourish the skin with concentrated nutrients including which may prove beneficial in treating inflammatory conditions of the skin such as acne, psoriasis, eczema and rosacea. The antioxidant properties may prove to have some of the most effective rejuvenating properties of any known topical skin treatment to date. (Dr. Charles Crutchfield, Assoc. Prof. of Dermatology, et. al., Univ. of Minnesota).

Anti Inflammation

Cox-2 inhibition activity of many NatureFRESH-Cold press fruit and herb oils according to laboratory assays conducted by Liangli Yu, PhD at the University of Maryland, are many times greater than aspirin. Cox-2 is an enzyme linked to inflammation and inflammation is associated with many skin disorders ranging from sunburn to roseacea, psoriasis, acne and dandruff.

Antioxidant Protection to the Power of 10

The NatureFRESH-Cold press process preserves the natural antioxidants in the botanical seed oils resulting in superior free radical quenching. Many of the botanical oils contain a broad mixture of Vitamin E isomers, often acting synergistically with other antioxidants that result in a total antioxidant level ten times, twenty times and even forty times or more than the fruit overall. The cranberry and raspberry fruit seed oils for example have rich concentrations of the tocotrienol form of Vitamin E. The tocotrienol forms of vitamin E are just now being scientifically understood. They are the less saturated form of Vitamin E, enabling them to move around more freely and efficiently in cell membranes where they intercept and neutralize free radicals than can the tocopherols. Research by noted scientists at the University of California discovered the tocotrienol form of Vitamin E can be 40-60 times more effective in neutralizing free radicals than alpha tocopherol.

Anti Microbial Activity

Many skin disorders are known to result from or are exacerbated by bacteria and fungi living on the surface of the skin. The antimicrobial activity of super potent antioxidant botanical oils is very strong enabling them to act as a bactericide against a broad range of microorganisms and even pathogens such as *E. coli* and listeria. Potent antioxidant botanical oils have been shown in research at the University of Maryland to not only inhibit growth of a broad range of microorganisms but also to reduce them to a zero survival rate.

There's an old saying, the best approach is to mimic nature as nature knows best. So, when it comes to protection for the skin, NatureFRESH-Cold Press oils seem to work well. The NatureFRESH Cold press oils have the right combinations and right mixtures of antioxidants, essential fatty acids and nutrients to protect and nourish the skin in multiple ways. Hopefully, more skin care specialists will realize the potential of these natural ingredients and use them in their daily patient treatment programs.

In *The Use of Nature Fresh Cold Pressed Seed Oils for Skin and Personal Care Products—A New Approach* article, there is discussion about research showing that synergistic botanic seed oils can inhibit Cox-2 activity. Cox-2 is an enzyme linked to inflammation and inflammation is associated with many skin disorders ranging from sunburn to roseacea, psoriasis, acne and dandruff. In addition, the article discusses research that synergistic botanic seed oils have potent antimicrobial activity. Many skin disorders are known to result from or be exacerbated by bacteria and fungi living on the skin surface.

Concentrated plant seed oils are an excellent source of antioxidants. In addition to traditional antioxidants, such as vitamins C and B, plant seed oils contain phenolic compounds which are excellent free radical scavengers. Black raspberry and red raspberry seed oils have a diversity and ultra-rich content of antioxidants, including 4 different forms of Vitamin E (Alpha and Gamma Tocopherol, Beta and Gamma Tocotrienol). These raspberry seed oils contain Omega 3 and Omega 6. In U.S. Patent Publication No. 20070243310, Synergistic super potent antioxidant cold pressed botanic oil blends, to Leonard et al., published Oct. 18, 2007, the inventors describe blends of seed oils as having a synergistic antioxidant effect.

Concentrated seed oils are described as immunostimulants in U.S. Patent Publication No. 2007/0128301, Immune Enhancement by Seed Oil and/Or Seed Flour, to Saltzman et al, published Jun. 7, 2007, and for use in treatment of cancer in Patent Publication No. 2005/0244375, Composition and Method of Cancer Treatment, to Leonard et al, published Nov. 3, 2007. In Saltzman et al., the applicant theorized that concentrated seed oils possess anti-inflammatory properties.

The concentrated plant seed oils used in the improved topical skin care composition of the invention are prepared according to a cold press method. A preferred method of preparing the botanic seed oils, used in the invention, is described in U.S. Patent Publication No. 2007/0128301, Immune Enhancement by Seed Oil and/Or Seed Flour, Saltzman et al., published Jun. 7, 2007, U.S. Patent publication is incorporated by reference herein in its entirety. That description is:

"The oils for the composition are prepared from seeds which have been carefully dried and cleaned at temperatures below 120 degrees F. In a cold press process, the seeds are fed through the press and put under high pressure with no extra heat during the pressing process. Oil temperatures during extraction are typically 70 degrees to 90 degrees F. To insure minimal or no oxidation and the highest potential antioxidant level of the oils, the press head and oil extraction chamber can be enclosed within an inert atmosphere. Refining or removal of suspended solids and container filling can also be done in an inert atmosphere to preserve quality."

U.S. Patent Publication No. 2007/0128301, paragraph [0016].

Example 1

The inventor used CeraVe® brand of skin lotion as a base skin care composition suitable for application to skin having a multivesicular emulsion skin care delivery system, prepared according to Espinoza. The inventor prepared an improved skin lotion with 99.4% (% w/w) CeraVe® lotion, 0.5% (% w/w) red raspberry seed oil prepared according to a cold press method, blended with 0.0125% (% w/w) of each of the following seed oils, prepared according to a cold press method: pumpkin seed oil, chardonnay grape seed oil, carrot seed oil, blueberry seed oil, cranberry seed oil, pomegranate seed oil, black cumin seed oil, and black raspberry seed oil.

A preferred composition of the improved skin lotion involves blends having a plurality of concentrated seed oils. Not to be bound by theory, but it is believed that such blends of concentrated seed oils have a synergistic antioxidant effect that is beneficial for treatment of skin conditions.

A range in the improved skin care composition of about 0.1% (% w/w) to about 2% (% w/w) of the complete blend of seed oils, prepared according to a cold press method, can be used, while a narrower range of about 0.5% (% w/w) to about 1% (% w/w), prepared according to a cold press method, in the above proportions is more suitable.

A range in the improved skin care composition of about 0.5% (% w/w) to about 1% (% w/w) of red raspberry seed oil, prepared according to a cold press method is a preferred embodiment.

The range of skin lotion as a base skin care composition suitable for application to skin having a multivesicular emulsion skin care delivery system is about 98.% (% w/w) to about 99.9% (% w/w), while a narrower range of about 99% (% w/w) to about 99.5% (% w/w) is more suitable.

Under the inventor's supervision, 110 patients with rosacea were treated with the improved skin lotion having 99.4% CeraVe® lotion, 0.5% red raspberry seed oil, prepared according to a cold press method, blended with 0.0125% of each of the following seed oils prepared according to a cold press method: pumpkin seed oil, chardonnay grape seed oil, carrot seed oil, blueberry seed oil, cranberry seed oil, pomegranate seed oil, black cumin seed oil, and black raspberry seed oil. Ninety percent (90%) of the patient report a positive response to the treatment.

Under the inventor's supervision, 100 skin rejuvenation patients were treated with the improved skin lotion having 99.4% CeraVe® lotion, 0.5% red raspberry seed oil, prepared according to a cold press method, blended with 0.0125% of each of the following seed oils prepared according to a cold press method: pumpkin seed oil, chardonnay grape seed oil, carrot seed oil, blueberry seed oil, cranberry seed oil, pomegranate seed oil, black cumin seed oil, and black raspberry seed oil. Seventy percent (70%) of the patient reported a preference for the improved skin lotion with the botanic seed oils of the invention over Prevage® brand of non-medicated anti-aging cream, a leading over the counter cream. Prevage® is a trademark owned by Allergan, Inc. Corporation Delaware 2525 Dupont Drive Irvine Calif. 92612.

Prophetic Examples

Espinoza disclosed that preparation in a particular way assures an multivesicular emulsion skin care formulation. In Example 1 (above), the inventor used CeraVe® lotion. The CeraVe®lotion was prepared according to the patented technology for that lotion. Example 1 (above), added the blends of botanic seed oils, prepared according to a cold press method, to the already prepared CeraVe® lotion.

The inventor envisions that a multivesicular skin care delivery system, prepared in the manner described in Espinoza, will exhibit similar useful properties for dermatologic conditions. The inventor proposes that the blends of botanic seed oils, prepared according to a cold press method, be used in the active mixing described in Espinoza, Col. 7, lines 47-62, inter alia, as follows:

"According to the method, the active is mixed with all other compatible members of its phase. By compatible members, it is meant those that it will dissolve in. For example, if the active is water soluble, it would be the water phase of the emulsion system. On the other hand, if the active is oil soluble and water insoluble, it would be mixed with the oil phase of the system. After this mixing occurs, the active and the rest of the system, i.e. the base, are then high-shear mixed with the multivesicular emulsifier such as behentrimonium methosulfate until visual inspection reveals that one does has a multivesicular emulsion. Typically, this will take from 5 to 30 minutes in a mixer such as a turbine type propeller mixer or Cowles Dissolver."

Under this prophetic example, the blends of botanic seed oils, would then be mixed at the appropriate stage, then the active and the rest of the system, i.e. the base (as term is used in the Espinoza patent) would be high-shear mixed as described in Espinoza. The prophetic examples could replace the percentage of oils shown in the Espinoza Sample formulations with an effective therapeutic amount of the blends of botanic seed oils, described above, to create a skin care composition. For example, several sample formulations in Espinoza use oils, including but not limited to sunscreen lotion, marine botanical cream, and ceramide cream. A range in the improved skin care composition of about 0.1% (% w/w) to about 2% (% w/w) of the complete blend of seed oils, prepared according to a cold press method, would be a range for use. A therapeutically effective amount of the blends of botanic seed oils, prepared according to a cold press method, would be a range from about 0.1% (% w/w) to about 5% (% w/w) of the total composition.

Not to be bound, by theory, but it is anticipated that a preferred range for use of the blends of botanic seed oils, prepared according to a cold press method, would be lower than the about 5% (% w/w) of the total composition. This extrapolation is based on the synergistic properties of blends of botanic oils, prepared according to a cold process method.

A person skilled in the art would be able to adjust the other ingredients in the formulation based on use of the selected percentage of the blends of botanic seed oils, prepared according to a cold press method.

The above invention envisions other topical skin compositions, such as creams and gels, having a base composition suitable for application to skin with a multivesicular emulsion skin care delivery system, said base composition further blended with botanic seed oil, prepared according to a cold press method, having red raspberry seed oil, and a plurality of oils selected from the group consisting of the following seed oils: pumpkin seed oil, chardonnay grape seed oil, carrot seed oil, blueberry seed oil, cranberry seed oil, pomegranate seed oil, black cumin seed oil, and black raspberry seed oil. A person of skill in the art would be able to modify and prepare such compositions using the disclosure.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An improved topical skin care composition comprising: a base skin lotion suitable for application to skin having a multivesicular emulsion skin care delivery system, the base skin care composition is about 99.4% (w/w) of the improved topical skin composition; and blends of botanic seed oil, prepared according to a cold press method, having red raspberry seed oil about 0.5% (w/w) blended with about 0.0125% of each of the following seed oils: pumpkin seed oil, chardonnay grape seed oil, carrot seed oil, blueberry seed oil, cranberry seed oil, pomegranate seed oil, black cumin seed oil, and black raspberry seed oil.

2. An improved topical skin care composition comprising: a base skin lotion suitable for application to skin having a micelle skin care delivery system, the base skin care lotion is about 99.4% (w/w) of the improved topical skin composition; and blends of botanic seed oil, prepared according to a cold press method, having red raspberry seed oil about 0.5% (w/w) blended with about 0.0125% of each of the following seed oils: pumpkin seed oil, chardonnay grape seed oil, carrot seed oil, blueberry seed oil, cranberry seed oil, pomegranate seed oil, black cumin seed oil, and black raspberry seed oil.

* * * * *